(12) United States Patent
Priewe et al.

(10) Patent No.: US 7,615,065 B2
(45) Date of Patent: Nov. 10, 2009

(54) AREAL IMPLANT

(75) Inventors: Jörg Priewe, Kiel (DE); Birgit Hartkop, Berkenthin (DE); Barbara Schuldt-Hempe, Bad Bramstedt (DE); Christoph Walther, Kattendorf (DE); Jörg Holste, Norderstedt (DE)

(73) Assignee: Ethicon Inc., Somerville, NJ (US)

( * ) Notice: Subject to any disclaimer, the term of this patent is extended or adjusted under 35 U.S.C. 154(b) by 501 days.

(21) Appl. No.: 10/495,400

(22) PCT Filed: Nov. 12, 2002

(86) PCT No.: PCT/EP02/12652

§ 371 (c)(1),
(2), (4) Date: May 12, 2004

(87) PCT Pub. No.: WO03/041613

PCT Pub. Date: May 22, 2003

(65) Prior Publication Data

US 2005/0010306 A1    Jan. 13, 2005

(30) Foreign Application Priority Data

Nov. 14, 2001  (DE)  ................ 101 55 842

(51) Int. Cl.
*A61B 17/08* (2006.01)
*A61F 2/02* (2006.01)

(52) U.S. Cl. .................... 606/154; 623/23.75

(58) Field of Classification Search ............ 606/151, 606/154, 213, 215, 233; 623/23.75, 1.13
See application file for complete search history.

(56) References Cited

U.S. PATENT DOCUMENTS

| 4,762,751 A | * | 8/1988 | Girgis et al. ................. 428/378 |
| 5,514,181 A | * | 5/1996 | Light et al. ............... 623/13.18 |
| 5,686,090 A |   | 11/1997 | Schilder et al. |
| 5,693,085 A | * | 12/1997 | Buirge et al. ................ 623/1.13 |
| 5,735,897 A | * | 4/1998 | Buirge ........................ 623/1.15 |
| 5,743,917 A |   | 4/1998 | Saxon |
| 5,843,166 A | * | 12/1998 | Lentz et al. ................. 623/1.13 |
| 6,139,573 A | * | 10/2000 | Sogard et al. ............... 623/1.13 |
| 6,162,962 A | * | 12/2000 | Hinsch et al. ............. 623/11.11 |

(Continued)

FOREIGN PATENT DOCUMENTS

EP    1099421 A    6/2001

(Continued)

OTHER PUBLICATIONS

Dinsmore, R.C. et al 'Prevention of Adhesions to Polypropylene Mesh in a Traumatized Bowel Model', J. Am. Coll. Surg. vol. 191, No. 2 (2000) pp. 131-136.
Simon, E. et al Acta Chirurgica Hungarica 38(2)(1999), pp. 205-207.

*Primary Examiner*—Thomas J Sweet
(74) *Attorney, Agent, or Firm*—Emil Richard Skula

(57) ABSTRACT

An areal implant has a long-term-stable, mesh-like basic structure which has pores of a size in the range from 1.5 mm to 8 mm and is provided, at least in a part area, on both sides with a synthetic, resorbable polymer film. The two polymer films are glued or welded together in pores of the basic structure.

5 Claims, 1 Drawing Sheet

U.S. PATENT DOCUMENTS

| | | |
|---|---|---|
| 6,264,702 B1 | 7/2001 | Ory et al. |
| 6,579,314 B1 * | 6/2003 | Lombardi et al. .......... 623/1.44 |
| 6,709,455 B1 * | 3/2004 | Chouinard ................. 623/1.32 |
| 6,852,330 B2 * | 2/2005 | Bowman et al. ............ 424/426 |
| 7,175,591 B2 * | 2/2007 | Kaladelfos ................... 600/37 |
| 2002/0119177 A1 * | 8/2002 | Bowman et al. ............ 424/423 |
| 2004/0059356 A1 * | 3/2004 | Gingras ...................... 606/151 |
| 2005/0060020 A1 * | 3/2005 | Jenson ...................... 623/1.13 |

FOREIGN PATENT DOCUMENTS

| | | |
|---|---|---|
| JP | 03295561 | 12/1991 |
| WO | WO 90/00410 | 1/1990 |
| WO | WO 93/17635 | 9/1993 |
| WO | WO 99/51163 | 10/1999 |
| WO | WO 00/67663 | 11/2000 |
| WO | WO 0115625 A | 3/2001 |
| WO | WO 01/43789 | 6/2001 |

\* cited by examiner

AREAL IMPLANT

CROSS-REFERENCE TO RELATED CASES

This application is a 371 of international application serial number PCT/EP02/12652 filed on Nov. 12, 2002, which claims the benefit of German application no. 10155842.2 filed Nov. 14, 2001.

BACKGROUND OF THE INVENTION

The invention relates to an areal implant and a process for the manufacture of such an implant.

Often, after the intraperitoneal implantation of polymer meshes, adhesions of internal structures occur, such as intestine, omentum, etc. Possibilities have therefore been sought for years of preventing adhesion in the area of the implant, both in the centre and the periphery, or at least to reduce its intensity.

An implant marketed by Gore under the name Dualmesh®, which is not a mesh, but a PTFE membrane, has pores on one side in order to facilitate a better tissue integration. With regard to adhesions, this implant displays favourable behaviour; it is not incorporated sufficiently into the tissue, however.

The Sepramesh® implant from Genzyme is a heavyweight polypropylene mesh which contains a film consisting essentially of natural substances (carboxymethylcellulose and hyaluronic acid) but which is brittle.

Sofradim markets under the name Parietex-Composite® a polyester mesh coated with bovine collagen which has its own problems caused by BSE and proteins not occurring naturally in the body and cannot be cut to size according to the manufacturer's instructions.

U.S. Pat. No. 6,162,962 mentions that implantable polymer meshes can also be strengthened with resorbable films, but discloses no method for the preparation of large-pored meshes which are connected in a sufficiently stable manner to a thin, sensitive, resorbable polymer film. Furthermore, there is no mention of an intraperitoneal application or reference to the reduction of adhesions.

WO 93/17635 shows two-layered composite implants which consist of a porous layer, which is to promote the growing-in of tissue and also to bring about an inflammatory reaction, and a barrier, which is intended to counteract postoperative adhesions.

JP 03295561 discloses films, which contain collagen, have a mesh-like structure and are intended to prevent adhesions.

R. Dinsmore et al. (J. Am. College of Surgeons 191(2), pp. 131-6 (August 2000)) describe the reduction of adhesions with the help of "Seprafilm" (Genzyme), a mixture of a natural product and a modified natural product (hyaluronic acid and carboxymethylcellulose), during the treatment of abdominal wall defects with a polypropylene mesh. "Seprafilm" has the disadvantage that it is relatively brittle when dried and has to be pre-wetted before the surgery.

WO 99/51163 shows resorbable polymer meshes which are covered with different resorbable polymer layers, the second layer being intended to resorb more slowly.

WO 90/00410 describes the reinforcing of polymer films with partly or completely resorbable polymers.

WO 00/67663 discloses a hernia-repair mesh that contains an incision and is covered at one end with a membrane which is intended to prevent the adhesion of the spermatic cord. Such a mesh cannot be used for abdominal wall defects due to the incision and cannot be cut to size everywhere.

U.S. Pat. No. 5,743,917 describes non-resorbable, heavy-weight polypropylene meshes customary in the trade, which are covered with a non-resorbable layer of PTFE which is not to be incorporated into the tissue.

WO 01/43789 shows meshes layered with hyaluronic acid and carboxymethylcellulose.

SUMMARY OF THE INVENTION

It is the object of the invention to provide a well tolerated areal implant which reduces the formation of fusions (adhesions) of internal structures in human or animal organisms, but also facilitates the growing-in of the tissue naturally occurring in the body after a short time.

DETAILED DESCRIPTION

Figure 1:
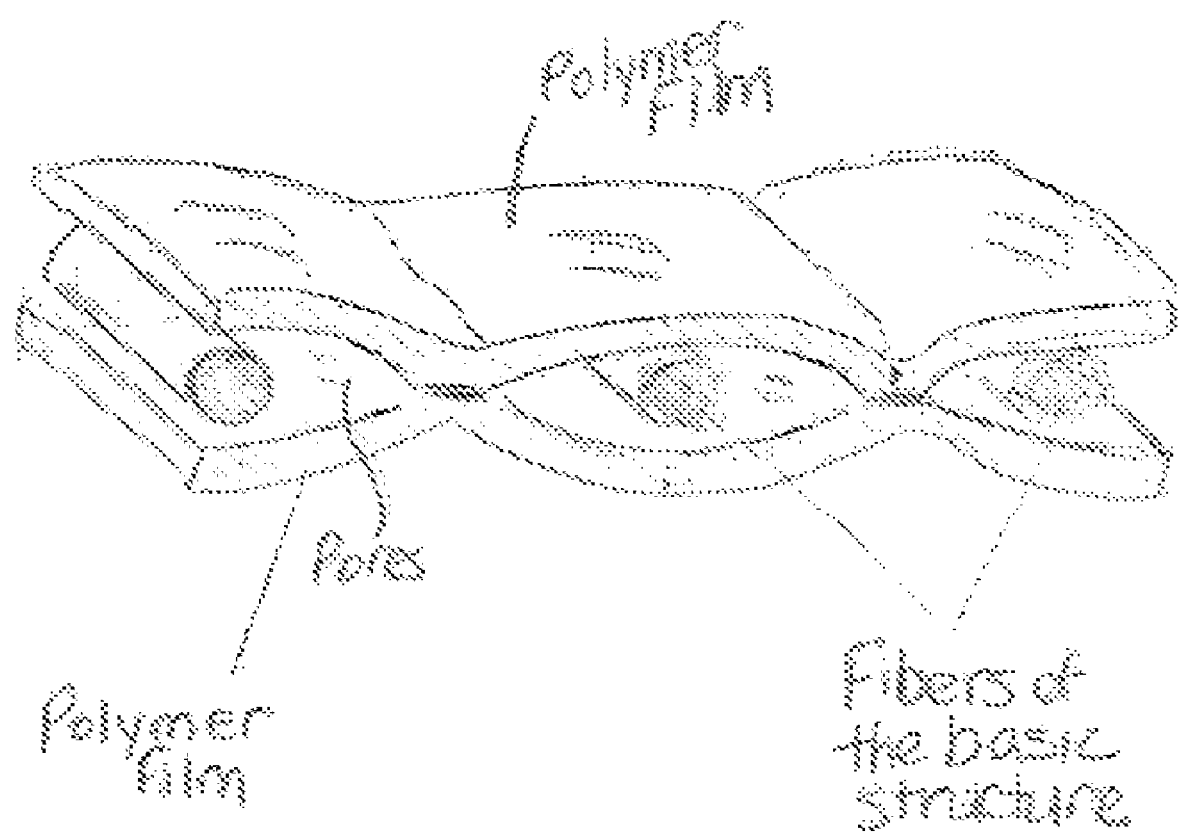
FIG. 1 illustrates an exemplary embodiment having films on both sides of the basic structure coupled together through pores of the basic structure.

The areal implant according to the invention has a long-term-stable, mesh-like basic structure with pores, the size of which over more than 90% of the total area of the pores lies in the range from 1.5 mm to 8 mm. The basic structure is provided, at least in a part area, on both sides with a synthetic, resorbable polymer film, the two polymer films being glued or welded together in pores of the basic structure. The pore size is the 25 greatest width of the respective pore of the mesh-like basic structure.

As the two polymer films are glued or welded together in pores of the basic structure, the individual layers of the implant according to the invention are reliably connected to each other. Depending on the type of materials used, the polymer films can additionally also be glued or welded to the basic structure.

In contrast to the view that a porous and a smooth side are needed in order to support the growing-in of tissue on one side of the implant and to reduce the tendency to adhesions on the other side, a polymer film is provided on both sides in the case of the implant according to the invention. The advantage of this is that a barrier is present in the first phase after implantation on both sides which minimises adhesions. After some days or weeks (e.g. when the pseudoperitoneum has formed) this barrier breaks up, however, upon resorption of the polymer films, and tissue can grow in.

A further advantage when using the implant according to the invention is that if both sides of the implant are of the same design, consideration need not be given to which side, e.g., is to face the intestine. Thus there is no danger of confusing the two sides, and cumbersome techniques such as are used with some conventional implants (manual marking of one side directly before implantation) become superfluous.

Due to the relatively large pores, the implant according to the invention is as a rule light and thus well tolerated. The entire area of the pores preferably accounts for at least 50% of the basic area of the mesh-like basic structure.

There are many possibilities for the arrangement of the two opposite-facing films or film pieces. For example, the film pieces need not be congruent. It is also conceivable that several sections are present on the mesh-like basic structure in which the basic structure is provided with a synthetic, resorbable polymer film on both sides. In a preferred version, the basic structure is provided with polymer film on both sides in its central section, while it lies exposed in an edge area.

Furthermore, polymer film can project beyond the edge of the basic structure at least on one side of the basic structure and at least in one edge area of the basic structure. In one version the basic structure is completely enclosed between two layers of polymer film which extend beyond the edge of the basic structure and are there connected to each other. The polymer films can be closed (i.e. without pores) but can also have openings, at least in a part area.

In a preferred version, at least in a part area of the basic structure, the polymer films are connected over their whole surface to the basic structure or the respective polymer film on the opposite side, but a pointwise connection is also conceivable.

The basic structure can contain, in addition to a long-term stable polymer, a resorbable polymer, the resorbable and the long-term stable polymer preferably containing monofilaments and/or multifilaments.

By a long-term-stable polymer is meant a non-resorbable polymer or a very slowly resorbable polymer which still possesses at least 50% of its original tearing strength 60 days after the implantation. The latter group also includes substances such as e.g. polyamide, which generally are regarded as resistant, as they are not designed as resorbable material, but are attacked over time by body tissue and tissue fluids. Particularly preferred materials for the basic structure are polypropylene and mixtures of polyvinylidene fluoride and copolymers of vinylidene fluoride and hexafluoropropene, but other materials are also conceivable. Both monofilaments and multifilaments come into consideration.

Particularly suitable materials for the polymer films are poly-p-dioxanone, copolymers of glycolide and lactide (e.g. in the ratio 9:1) and mixtures of poly-p-dioxanone and polyethylene glycol, but other synthetic, resorbable materials are also possible.

The basic structure is preferably weft-knitted or warp-knitted. Preferred thicknesses for the polymer films lie in the range from 10 μm to 300 μm, in particular between 10 μn and 50 μm.

In the case of an intraperitoneal application of the implant according to the invention, adhesions are very largely prevented and after a short time tissue naturally occurring in the body has grown through the implant, which is covered by a new peritoneum (pseudoperitoneum).

Surprisingly, in particular lightweight, large-pored, thin, flexible, non-resorbable polymer meshes which are bound on both sides with only a thin, resorbable, synthetic polymer film can be prepared simply, well and with sufficient stability. These implants are easily cut to size. The adhesion of internal organs is largely prevented in the central region and also in the edge area of the implant. It is particularly advantageous if the polymer film covers a peritoneal defect in the abdominal wall only in the central area of the basic structure. In addition, the implants display good handling properties in the non-resorbed state and a certain shape memory, so that they can be easily unfolded even after a trocar passage. Further advantages are the biocompatibility, the minimized allergenic potential (as only synthetic polymers are used) and the low risk of infection, which can pose a problem with natural substances, such as proteins or sugars.

Along with these properties the implants according to the invention are characterized in that tissue grows surprisingly quickly and well into the implant. This is caused by the fact that, although the actual resorption of the polymers of the resorbable films can last some months, the integrity and the stability of the films is already reduced after less than 4 weeks with the preferred materials and these decompose into small fragments between which new tissue can grow in. No very quickly decomposing polymers, which would release a high local amount of metabolites (e.g. lactic acid or glycolic acid) in a short time, are necessary, but tissue integration and polymer decomposition are essentially uncoupled, so that wound-healing processes and the development of a new peritoneum over the implant can take place largely undisturbed.

The invention is explained further in the following using embodiments.

EXAMPLES

Example 1

Polydioxanone Film on Mesh on Both Sides

A mesh was prepared as a mesh-like basic structure of an implant from 3-mil-thick Pronova® monofilaments (1 mil=0.0254 mm) in warp and two part-wefts on a Muller 8-feed Raschelina RD3MT3 420 SN type laboratory machine. Pronova® (Ethicon) is a mixture of polyvinylidene fluoride and a copolymer of vinylidene fluoride and hexafluoropropene. The needles of the machine were laid 1 full/1 empty and the threads worked with a stitch density of 18.6 stitches/cm. A piece of this mesh measuring 10 cm by 10 cm was thermally fused on both sides, each with a round film (diameter 6 cm) of poly-p-dioxanone of 25 μm thickness, such as is used for the Ethicon product "Durapatch". The upper hot plate had a temperature of somewhat over 100° C., the lower hot plate one of under 70° C. After being kept for approx. 2 minutes under slight pressure and then cooled, the sample, which lay below on several layers of baking paper and was covered above with one layer, was removed from the hot press.

An implant resulted which was partially enclosed in very largely hole-free film, displayed no sharp-edged transitions between mesh and film, and could be easily cut to size in the edge area without becoming sharp-edged in the process.

Example 2

Whole-surface Both-side Polydioxanone Film on Mesh

A piece of mesh-like basic structure measuring 10 cm by 10 cm prepared as in Example 1 from Pronova® monofilaments (pattern notation see Table 1) was thermally gummed on both sides over the entire surface with a square, 25-μm-thick film of poly-p-dioxanone (length and width in each case 10 cm) as is used in the product "Durapatch" (Ethicon).

An implant resulted which was completely enclosed in hole-free film.

Example 3

Whole-surface Both-side Polydioxanone Film on Mesh

A piece of mesh-like basic, structure measuring 10 cm by 10 cm prepared as in Example 1 from Pronova® monofilaments (pattern notation see Table 1) was thermally gummed on both sides over the entire surface with a square, 25-μm-thick film of poly-p-dioxanone (length and width in each case 15 cm) as is used in the product "Durapatch" (Ethicon).

An implant resulted which was completely enclosed in hole-free film, the bound films overlapping the mesh area at the edges by approx. 2.5 cm.

Example 4

Pronova® Mesh with Both-side Film

A mesh was prepared as a mesh-like basic structure of an implant from 3.5 mil-thick Pronova® monofilaments (1 mil=0.0254 mm) in warp and two part-wefts on a Muller 8-feed Raschelina RD3MT3 420 SN type laboratory machine. The needles of the machine were laid 1 full/1 empty and the threads worked with a stitch density of 18.6 stitches/cm. The associated pattern notation given in Table 1 shows the design and the course of the thread.

A piece of this mesh measuring 5 cm by 9 cm was thermally fused on both sides, each with a rectangular film measuring 3 cm by 7 cm made from poly-p-dioxanone of 25 μm thickness, such as is used for the Ethicon product "Durapatch", so that a film-free edge area of approx. 1 cm width formed. The upper hot plate had a temperature of somewhat over 100° C., the lower hot plate one of under 70° C. After being kept for approx. 2 minutes under slight pressure and then cooled, the sample, which lay below on several layers of baking paper and was covered above with one layer, was removed from the hot press.

An implant resulted which was partially enclosed in very largely hole-free film, displayed no sharp-edged transitions between mesh and film and could be easily cut to size in the edge area without becoming sharp-edged in the process.

Example 5

Polypropylene Mesh with Both-side Film

The mesh-like basic structure of an implant was prepared as in Example 4, but with the difference that Pronova® was not used as material but a polypropylene monofilament of 3.5 mil thickness. Pattern notation, structure and the course of the thread can again be seen in Table 1.

A piece of this mesh measuring 5 cm by 8 cm was thermally fused as in Example 4 on both sides, each with a round film (diameter 6 cm) of poly-p-dioxanone of 25 μm thickness. An implant resulted which was partially enclosed in very largely hole-free film, displayed no sharp-edged transitions between mesh and film and could be easily cut to size in the edge area without becoming sharp-edged in the process.

TABLE 1

Pattern notations for the Examples 1 to 5

| Examples 1 to 3 | Examples 4 and 5 |
| --- | --- |
| Warp: closed pillar stitch<br>Wefts:<br>L1: 6-2/6-2/6-4/8-4/8-4//<br>L2: 2-6/2-6/2-4/0-4/0-4// | Warp: closed pillar stitch<br>Wefts:<br>L1: 2-4/2-4/0-4/2-4/2-6//<br>L2: 4-2/4-2/6-2/4-2/4-0// |

Example 6

Mixed Polydioxanone/PEG Film on Mesh

A mixed film of poly-p-dioxanone, such as is used in the product "Durapatch" (Ethicon), and polyethylene glycol (PEG; molecular weight 3350) with a PEG content of 20 wt-% was prepared by melting, mixing and thermal pressing. The film had a thickness of approx. 60 μm-100 μm and appeared macroscopically homogeneous.

A part of the film was cut into pieces measuring 0.5 cm by 2 cm and the film pieces were placed on a piece of baking paper, 2 cm apart from each other. A "Vypro" mesh (Ethicon GmbH; composite mesh of polypropylene and, as resorbable part, Vicryl®, a copolymer of glycolide and lactide in the ratio 9:1) cut to 10 cm by 10 cm was placed thereon, and the intact remaining film onto this. Then, a pressure was exerted at a temperature of approx. 120° C. for some minutes. An implant resulted in which the composite mesh serving as mesh-like basic structure was securely anchored to the film pieces.

Example 7

Composite Prepared from Perforated Film, Mesh and Film

The procedure was analogous to that of Example 2 with the difference that holes of 0.5 cm diameter with a hole-to-hole distance of 1 cm were punched out of one film in order to reduce the foreign material content.

The films were securely bonded to the mesh by a film-film bonding.

Example 8

Multifilament-light Mesh with Thin Film

The resorbable portion was removed from a "Vypro" mesh (Ethicon) customary in the trade by boiling in soda solution and repeated washing. The polypropylene light mesh thus obtained was covered on one side with 0.5 cm wide and 10 cm long strips of an approx. 25-μm-thick film of poly-p-dioxanone, the film strips being approx. 1.5 cm apart from each other. A 25-μm-thick film of poly-p-dioxanone was laid on the other side of the mesh, into which round holes of 0.5 cm diameter had already been punched with a distance of 1.0 cm between the hole edges, such that the film strips came to rest on the film areas of the perforated film. This arrangement was fused under the conditions of Example 1.

Example 9

Preliminary Test for Adhesion Tendency of Light-weight Meshes in the Animal Model In order to test the induction of intraabdominal adhesions, different implant meshes were examined in the animal model without peritoneal defect, these being the three meshes summarized in Table 2 which were not provided with films.

TABLE 2

Three implant meshes

| Mesh | Preparation | Type |
| --- | --- | --- |
| "Vypro N" | Hydrolysis from "Vypro" according to Example 8 | Large-pored (4.5 mm), lightweight polypropylene multi-filament mesh |
| Marlex ® | Market product (Bard) | Small-pored (0.15 mm), heavyweight polypropylene monofilament mesh |
| "Pronova ®" | Starting mesh Example 2 | Large-pored (6.5 mm), lightweight monofilament mesh |

Procedure: The standardized examination took place on 5 rabbits 15 (with on average a body weight of 2700 g) per mesh type and examination time. The implantation took place with meshes cut to a size of 5 cm by 6 cm using the IPOM technique (intra-peritoneal onlay mesh technique, see e.g. E. Simon et al., Acta Chirurgica Hungarica 38(2), pp. 205-7 (1999)). All manipulations on the animals were carried out under intravenous general anaesthesia. After positioning, shaving and desinfection a suprasymphyseal skin incision was made on both sides in the right and left lower abdomen. After preparation of the abdominal wall as far as the musculature, a muscle purse-string suture was applied using "Vicryl 3-0" (Ethicon) in the area of the three skin incisions. After the introduction of pneumoperitoneum, by means of a Verres cannula, to an intraabdominal pressure of 4 mm Hg, a trocar measuring 10/12 mm was introduced via the suprasymphyseal skin incision. After the introduction of a 10 mm/O° optic, two further trocars were introduced (right lower abdomen 5 mm trocar, left lower abdomen 10/12 mm trocar) with visibility. By drawing tight the purse-string suture with two equidirectional knots, an optimum sealing of the pneumoperitoneum was achieved and the trocar fixing with the residual thread was made possible. The placing of the meshes took place in the central upper abdomen, in order to guarantee a direct contact with the intestine. The mesh fixing took place at all four corners and in the middle of the long side using an endoscopic multi-stapler (Endopath®, Ethicon). After the relief of the pneumoperitoneum the fascia-muscular trocar wound was closed by drawing tight the previously applied purse-string suture. Skin closure was carried out with resorbable single-button "Vicryl® 3-0" sutures. Wound covering was carried out using Nobecutan® spray.

Adhesion determination: For the qualitative-clinical appraisal and estimation of adhesion formation, a control laparoscopy was carried out in a final anaesthesia. This involved the same technique as described above with appropriate documentation by means of a video unit. For the quantitative appraisal of the adhesions, following the opening of the abdominal cavity away from the mesh and the exposing of the area of the surgery, the outlines of the adhesions between abdominal wall and mesh and also of interenteric adhesions were drawn on a clear film. With the help of computer-aided planimetry, it was possible to calculate the precise adhesion area in this way.

Result: After 7, 21 and 90 days the adhesion areas given in Table 3 were determined.

TABLE 3

Adhesion areas of the three implant meshes in the rabbit model

| Mesh | 7 days (mm$^2$) | 21 days (mm$^2$) | 90 days (mm$^2$) |
| --- | --- | --- | --- |
| "Vypro N" | 155 | 34 | 122 |
| Marlex ® | 1002 | 952 | 744 |
| "Pronova ®" | 0 | 80 | 38 |

This result shows the general advantage of light meshes as re-gards reduced adhesion formation and serves as preliminary test for a defect model in which the adhesion-reducing effect of the implant according to the invention is demonstrated.

Example 10

Results in the Abdominal Wall Defect Model

Internal structures, such as the abdominal viscera, are usually covered by a cell layer, the peritoneum, which prevents adhesions. If the peritoneum is damaged, the implant must not only not produce adhesions, but must also reduce adhesions. Therefore in this model both abdominal wall peritoneum (parietal peritoneum) and intestine peritoneum (visceral peritoneum) were damaged.

Implantation: This model was carried out in the open technique on 5 rabbits per each implant type. The rabbits were prepared and anaesthetized for the surgery. The abdomen was shaved between costal arch and pelvic inlet. The rabbits were placed on the operating table in the dorsal position and, after positioning on a vacuum cushion, fixed at the extremities. The OP field that had been shaved was desinfected. Each rabbit was covered with sterile cover film and a small window was cut out in the implantation area. After a median skin incision to a length of approx. 8 cm between xiphoid and symphysis, the abdominal fascia was prepared on both sides of the incision to a total width of approx. 4 cm. After opening of the abdomen by median laparotomy to a length of approx. 6 cm an internal abdominal wall defect measuring approx. 20 mm by 60 mm was created by excision of a 1 cm-wide strip of peritoneum from both wound edges; part of the fascia transversalis was also removed. The peritoneum of the caecum was damaged with a swab by rubbing.

The meshes cut to a size of 40 mm by 80 mm, previously sterilized by ethylene oxide, were sewn into the defect onto the peritoneum in direct contact with the abdominal organs with "Prolene" suture material (Ethicon; polypropylene), thickness 3-0 (metric 2), by transmural sutures using the IPOM technique (intra-peritoneal onlay mesh). The laparotomy wound was continually closed with "PDS" suture material (Ethicon poly-p-dioxanone), thickness 3-0 (metric 2). Above this, the skin was closed in interrupted suture with "Monocryl" (Ethiconi monofilament of a copolymer of glycolide and lactide), thickness 3-0 (metric 2).

After 28 days the animals were killed and the area and thickness of the adhesions were appraised. The result is summarized in Table 4.

TABLE 4

Experimental results of the adhesion of uncoated light meshes and light meshes provided with film in the peritoneal defect model (28 days)

| Mesh | Preparation | Type | Adhesion area [%] |
| --- | --- | --- | --- |
| "Pronova ®" | See Table 1 | Monofilament light mesh | 48 ± 28 |
| "Pronova ®", partly coated with PDS (poly-p-dioxanone) | Mesh measuring 4 cm by 8 cm coated on both sides with PDS film measuring 3 cm by 7 cm, analogous to Example 4 | Monofilament light mesh covered on both sides with 25-μm film | 7 ± 4 |
| "Pronova ®", completely coated with PDS (poly-p-dioxanone) | Mesh measuring 4 cm by 8 cm coated on both sides with PDS film measuring 4 cm by 8 cm, original mesh prepared analogous to Example 4, but whole surface coated | Monofilament light mesh covered on both sides with 25-μm film | 9 ± 7 (only four rabbits here) |

Results: The light meshes coated with thin film (implants according to the invention) show a reduction in adhesion of over 80%, compared with the uncoated mesh, which in the already better by orders of magnitude than a heavy mesh customary in the trade (Marlex®). The degree of adhesion was lower with the implants according to the invention, so that the fusions could be more easily detached. In addition, a good growing-in of tissue was already seen after four weeks with these implants.

The invention claimed is:

1. A flat mesh surgical implant comprising
    a flat, biocompatible, polymeric mesh having first and second opposing sides, the mesh having an overall area, and having pores extending therethrough between the first and second opposing sides over more than 90% of the total area, wherein the pores range in size from 1.5 to 8 mm;
    a first synthetic, resorbable polymer film positioned adjacent the first side of the mesh, said first film having anti-adhesion properties; and
    a second synthetic, resorbable polymer film positioned adjacent the second side of the mesh, said second film having anti-adhesion properties,
    wherein the first and second polymer films are bonded to one another at a plurality of points passing through the pores of the mesh such that the mesh is not bonded to the first or second polymer films and such that the mesh is contained in a cavity between the films, and wherein the resulting implant has no pores extending therethrough, the flat mesh, first film and second film forming a flat mesh surgical implant, such that when the implant is implanted into a patient the first and second resorbable polymer films prevent surgical adhesions for a sufficiently effective period of time prior to resorbing, and tissue is subsequently allowed to grow into the pores of the flat mesh.

2. The implant according to claim 1, where the mesh is made from at least one material selected from the group consisting of: polypropylene, mixtures of polyvinylidene fluoride, copolymers of vinylidene fluoride and hexafluoropropene, and resorbable polymers.

3. The implant according to claim 1, where the polymer film is made from at least one of material selected from the group consisting of: poly-p-dioxanone, copolymers of glycolide and lactide, mixtures of poly-p-dioxanone and polyethylene glycol, mixtures with polyethylene glycol, and copolymers of the aforementioned substances.

4. The implant according to claim 1, where the polymer films have a thickness in the range from 10 µm to 300 µm.

5. The implant of claim 1 wherein each pore has an area and the implant has an area such that the combined area of all of the pores is equal to at least 50% of the mesh area.

* * * * *

UNITED STATES PATENT AND TRADEMARK OFFICE
CERTIFICATE OF CORRECTION

| | | |
|---|---|---|
| PATENT NO. | : 7,615,065 B2 | Page 1 of 1 |
| APPLICATION NO. | : 10/495400 | |
| DATED | : November 10, 2009 | |
| INVENTOR(S) | : Jorg Priewe | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (501) days Delete the phrase "by 501 days" and insert -- by 643 days --

Signed and Sealed this

Thirty-first Day of August, 2010

David J. Kappos
*Director of the United States Patent and Trademark Office*